United States Patent [19]

Neri et al.

[11] 4,314,946

[45] Feb. 9, 1982

[54] PROCESS FOR THE CONTINUOUS SEPARATION OF MALEIC ANHYDRIDE FROM PROCESS GASES

[75] Inventors: Amleto Neri; Sergio Sanchioni, both of Bergamo, Italy

[73] Assignee: Ftalital Prodotti Chimici Speciali S.p.A., Mailand, Italy

[21] Appl. No.: 130,440

[22] Filed: Mar. 14, 1980

[30] Foreign Application Priority Data

Mar. 20, 1979 [IT] Italy ................................ 48436 A/79

[51] Int. Cl.³ ........................................... C07D 307/60
[52] U.S. Cl. ............................................... 260/346.76
[58] Field of Search .................................... 260/346.76

[56] References Cited

U.S. PATENT DOCUMENTS 3,891,680  6/1975  Katsumoto et al. ............ 260/346.76

FOREIGN PATENT DOCUMENTS 2444824  4/1976  Fed. Rep. of Germany .
1415748  8/1934  United Kingdom .
1443411  7/1976  United Kingdom .

*Primary Examiner*—John M. Ford
*Assistant Examiner*—Bernard Dentz
*Attorney, Agent, or Firm*—Fisher, Christen & Sabol

[57] ABSTRACT

Process for the continuous separation of maleic acid anhydride from process gases from the catalytic oxidation of hydrocarbons, e.g., n-butane, in the steam phase. The process gases are treated with a solvent, which is a cycloaliphatic acid ester. Typically, the cycloaliphatic acid ester is a dialkyl ester, having 4 to 8 carbon atoms in each alkyl group, of hexahydrophthalic acid, tetrahydrophthalic acid, methyltetrahydrophthalic acid or methylhexahydrophthalic acid.

4 Claims, 2 Drawing Figures

PROCESS FOR THE CONTINUOUS SEPARATION OF MALEIC ANHYDRIDE FROM PROCESS GASES

BACKGROUND OF THIS INVENTION

1. Field of This Invention

This invention relates to the production of maleic anhydride from the process gases from the catalytic oxidation of a hydrocarbon in the steam phase.

2. Prior Art

Maleic anhydride has been produced by the catalytic oxidation in the steam phase of benzol (i.e., benzene), and occasionally also n-butane, butene and other $C_4$-fractions. According to known methods, the maleic anhydride is obtained from the process gases in the following manner.

First, the gases are cooled to a temperature of 55° to 60° C. Such temperature lies below the so-called thaw point of maleic anhydride, but still is above the thaw point of water, which for its part is a by-product of the reaction. In the benzene process approximately 50 to 60 percent of the maleic anhydride can be condensed from the process gases. The lower the condensation temperature which is chosen, the more the water contained in the gas will be bound by the condensing maleic anhydride, thus forming maleic acid. However, the formation of maleic acid is undesirable, since the maleic acid is a solid product and is poorly soluble in molten maleic anhydride. Such leads to plugging up of the apparatus, which, in turn, results in the loss of throughput and yield.

The uncondensated maleic anhydride is obtained in the form of maleic acid by washing the stream of gas with water. The maleic acid then has to be converted again by dehydration into the maleic anhydride. As a result of isomerization, fumaric acid may then also be formed which ultimately leads to a large loss of yield.

U.S. Pat. No. 3,891,680 describes carrying out the washing operation in esters formed from phthalic acid with $C_4$-$C_8$ alcohols. According to German O.S. 2,444,824, dibenzylbenzol is used as the wash fluid. Finally, British Pat. No. 1,443,411 describes polymethylbenzophenone as the wash fluid. However, such systems have grave defects, such as the washing fluid lacking stability, especially (i) in the case of phthalic acid ester which leads to additional expenditures of the replacement of the lost washing fluid, (ii) from the high cost for the washing fluid in the case of polymethylbenzophenone, and (iii) from the fact that both polymethylbenzophenone as well as dibenzylbenzol are solid at ambient temperature.

BROAD DESCRIPTION OF THIS INVENTION

It is an object of this invention to provide wash fluids or solvents for maleic acid anhydride which do not have the above-stated prior art disadvantages. Other objects and advantages of this invention are set out herein or obvious herefrom to one ordinarily skilled in the art. The objects and advantages of this invention are achieved by the process of this invention, namely by the use of a cycloaliphatic acid ester as the solvent(s) in the treatment step of the process gases from the catalytic oxidation of hydrocarbon in the steam phase.

Preferably, a dialkyl ester, having 4 to 8 carbon atoms in each alkyl group, of hexahydrophthalic acid, tetrahydrophthalic acid, methyltetrahydrophthalic acid or methylhexahydrophthalic acid is used as the cycloaliphatic acid ester. Most preferably the solvent is dibutyl hexahydrophthalate, diisobutyl tetrahydrophthalate, diisobutyl hexahydrophthalate or dihexyl methylhexahydrophthalate.

The use of the solvent or solvents according to this invention is particularly advantageous whenever the reaction gases from the catalytic oxidation of n-butane in the steam phase are used as the process gases. In such case, the water concentration in the process gases is much greater than for example in the case of a catalytic oxidation process starting out from benzol. Thus, in the case of the catalytic oxidation of n-butane, conditioned by the large content of water, it is only possible to separate 30 to 35 percent of the maleic acid anhydride by the prior art method of partial condensation. The remaining 65 to 70 percent then must be washed out using water as a solvent, and thus is obtained as maleic acid. At a great expenditure of energy and losses in yield, the maleic acid has to be separated from the water and dehydrated into maleic anhydride. The process of this invention does not suffer such disadvantages.

The process of this invention can be carried out in known apparatus. The process gases from the reaction can first be subjected to a partial condensation. Partially condensed or uncondensed process gases are introduced into at least one washing column. This may be, for example, a plate-type column or a column filled with Raschig rings.

The process gas is introduced into a first column. The solvent flows against the stream of gas and is loaded increasingly with the maleic anhydride. The temperature and the maleic anhydride concentration of the stream of gas at the same time drop, while the solvent is enriched more and more with maleic anhydride. Additional columns can follow the first column, being used in a corresponding manner. The border of the adsorption of the maleic anhydride is set by the thaw point of the water in the reaction gases. It is possible to wash out up to more than 98 percent of the maleic anhydride from the process gases without any notable formation of maleic acid.

The solvent-anhydride mixture containing 10 to 30 percent maleic anhydride in the solvent can be fed continuously or gradually to a fractionated distillation. The maleic anhydride is distilled off and the high boiling solvent (solvents) can be fed again into the adsorption column.

The solvents used according to this invention have a number of outstanding advantages. They are liquid at ambient temperature and their viscosity is relatively low. For example, the well known polymethylbenzophenone or dibenzylbenzols are solid at ambient temperature. The solvents according to this invention have high boiling points. At the adsorption temperature used for the maleic anhydride from the process gases, the solvents have only low steam pressures. As a result of gas saturation, only negligibly small quantities of solvents are lost. The solvents according to this invention also have high chemical stability. They can be separated again by distillation from maleic anhydride after the adsorption and they can again be returned into the adsorption process. With the phthalic acid ester, for example, used by U.S. Pat. No. 3,891,680, losses always occur which must be replaced. Finally, the affinity of the solvents according to this invention for water is negligibly small. The formation of maleic acid is therefore reduced to an insignificant level.

Other examples of usefuls solvents within the scope of this invention are dibutyl methylhexahydrophthalate, diisobutyl hexahydrophthalate, diamyl methylhexahydrophthalate, diamyl hexahydrophthalate, diisoamyl methylhexahydrophthalate, di-3-pentyl hexahydrophthalate, di-2-pentyl methylhexahydrophthalate, dihexyl hexahydrophthalate, dioctyl methylhexahydrophthalate, diisohexyl hexahydrophthalate, di-2-hexyl methylhexahydrophthalate, di-3-hexyl hexahydrophthalate, di-2-ethyl-1-butyl methylhexahydrophthalate, di-2-methyl-2-pentyl hexahydrophthalate, diheptyl methylhexahydrophthalate, diheptyl hexahydrophthalate, dioctyl hexahydrophthalate, di-tert.butyl tetrahydrophthalate, di-sec.butyl methyltetrahydrophthalate, dineopentyl tetrahydrophthalate, diamyl methyltetrahydrophthalate, diamyl tetrahydrophthalate, diisoamyl methyltetrahydrophthalate, di-2-pentyl tetrahydrophthalate, diheptyl methyltetrahydrophthalate, di-tertamyl tetrahydrophthalate, di-2-pentyl methyltetrahydrophthalate, di-2-methyl-1-pentyl tetrahydrophthalate, dihexyl methyltetrahydrophthalate, di-3-methyl-1-pentyl tetrahydrophthalate, di-2-hexyl methyltetrahydrophthalate, di-3-methyl-2-pentyl tetrahydrophthalate, di-2,3-dimethyl-1-butyl methyltetrahydrophthalate, dioctyl tetrahydrophthalate, di-2-ethyl-1-hexyl methyltetrahydrophthalate, and butyl-amyl tetrahydrophthalate.

DETAILED DESCRIPTION OF THIS INVENTION

As used herein, all parts, percentages and ratios are on a weight basis unless otherwise stated herein or otherwise obvious herefrom to one ordinarily skilled in the art. The following examples illustrate the preferred embodiments of this invention.

EXAMPLE 1

Figure 1:
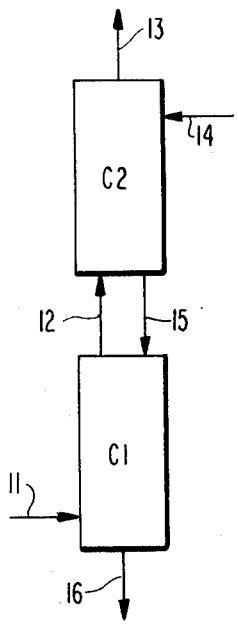

100 kg of off gases, from the catalytic oxidation reaction of n-butane to maleic anhydride, and also containing 2.65 kg of maleic anhydride and 4.8 kg of water, is fed to an absorption system composed of two columns as shown in the schematic flow diagram in FIG. 1. The off gases (line 11) enter first absorption column C1 at a temperature of 80° C. In column C1 the gases are scrubbed in a countercurrent manner with dibutylhexahydrophthalate at a temperature of 80° C. The gases leaving column C1 are cooled to 60° C. (by means of a heater exchanger not shown in FIG. 1) and enter (line 12) absorption column C2 having a temperature of 60° C. In column C2 the gases undergo once more a scrubbing operation with dibutylhexahydrophthalate, to such an extent that when they leave this column (line 13) their maleic anhydride content amounts to only 0.06 kg. The total maleic anhydride absorbed is 2.59 kg., with an absorption yield of 97.7 percent.

16.53 kg of solvent, containing 1.1 wt percent of maleic anhydride, is fed to the top of column C2 (line 14). At the outlet of column C2 there are 17.11 kg of maleic anhydride-dibutylhexahydrophthalate solution containing 4.4 percent of maleic anhydride (line 15). This solution, preheated at 80° C. (by heater exchanger not shown in FIG. 1), enters the top of column C1. At the outlet of column C1 (line 16) there are 19.12 kg of maleic anhydride-dibutylhexahydrophthalate solution, containing 14.5 wt. percent of maleic anhydride.

In column C1 the absorption of maleic anhydride amounts to 2.01 kg (77.6 percent of the absorbed maleic anhydride); in column C2 the absorption of maleic anhydride amounts to 0.58 kg (22.4 percent of the absorbed maleic anhydride). There are six theoretical absorption steps or plates (of which three are in column C1 and the remaining three are in column C2). The 14.5 percent maleic anhydride solution is sent to a fractional distillation system (not shown in FIG. 1), and practically pure maleic anhydride is obtained as the head product (2.59 kg) and dibutyl hexahydrophthalate containing 1.1 wt percent of maleic anhydride as the tail product. The resultant dibutyl hexahydrophthalate is recycled to the absorption system for the maleic anhydride through line 14.

EXAMPLE 2

Figure 2:
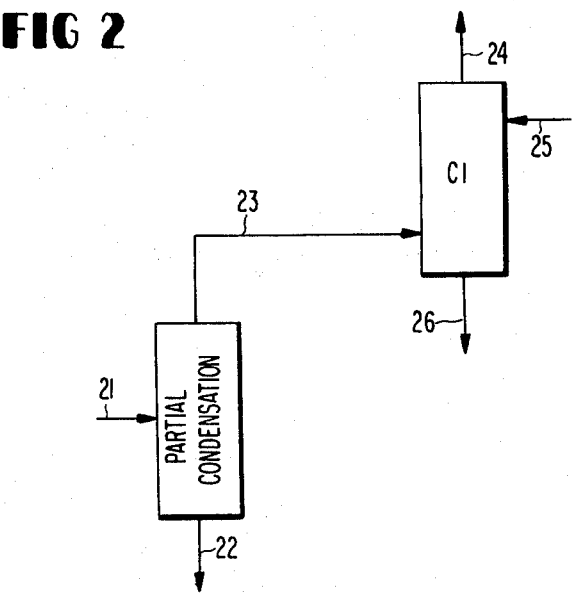

101.54 kg of off gases, (see FIG. 2) from the catalytic oxidation reaction of benzene to maleic anhydride (line 21), and also containing 2.96 kg of maleic anhydride and 2.82 kg of water, is sent to a system of partial condensation which, cooling the gaseous mixture to 58° C., causes condensation of 1.54 kg of maleic anhydride (line 22). The uncondensed gas (100 kg containing 1.42 kg of maleic anhydride) is passed (line 23) to the absorption column C1, scrubbed countercurrently with diisobutyltetrahydrophthalate, at a temperature of 58° C. The gases leaving the column (line 24) contain only 0.07 kg of maleic anhydride; the remaining 1.35 kg of maleic anhydride has been absorbed in diisobutyltetrahydrophthalate. The absorption yield is 95.1 percent. Therefore, the total yield of recovered maleic anhydride, considering that 1.54 kg. of maleic anhydride had been obtained directly through partial condensation, is 97.6 percent. There are four theoretical absorption steps in column C1 (FIG. 2).

8.25 kg of a maleic anhydride-diisobutyltetrahydrophthalate solution, containing 1.1 wt percent of maleic anhydride, is fed to the top of the column (line 25). The solution, rich in maleic anhydride (line 26) and containing 15 wt percent of maleic anhydride, weighs 9.60 kg. The solution undergoes separation by fractional distillation (not shown in FIG. 2). The resultant product composes 1.35 kg of almost pure maleic anhydride as the head fraction and 8.26 kg of maleic anhydride-diisobutyltetrahydrophthalate, with 1.1 wt. percent of maleic anhydride, as the tail fraction. The latter solution is returned for recycle to column C1 via line 25, whereas the almost pure maleic anhydride obtained as the head fraction is added to the maleic anhydride obtained through partial condensation (line 22) and distilled once again in order to obtain practically pure maleic anhydride.

EXAMPLE 3

100 kg of off gases, from the catalytic oxidation reaction of isomer n-butenes to maleic anhydride, and also containing 3.06 kg of maleic anhydride and 4.97 kg of water, is sent to an absorption system consisting of two columns as represented in the schematic flow diagram in FIG. 1. The temperature of the gas entering (line 11) first absorption column C1 is 75° C. In column C1 the gas undergoes countercurrent scrubbing with diisobutylhexahydrophthalate at a temperature of 75° C. The gases leaving column C1 are cooled down to 65° C. (by means of a heater exchanger not shown in FIG. 1) and enter (line 12) absorption column C2, which operates at 65° C. In column C2 the gases are ulteriorly washed with diisobutylhexahydrophthalate, so that the gases leaving column C2 contain only 0.06 kg of maleic anhydride. The total maleic anhydride absorbed is 3.00 kg, with an absorption yield of 98 percent. The solvent fed to the top of column C2 (line 14) amounts to 28.42 kg having a maleic anhydride content of 0.5 weight percent.

At the outlet of column C2 there are 28.79 kg of maleic anhydride-disobutylhexahydrophthalate solution containing 1.77 wt percent of maleic anhydride (line 15). This solution, preheated at 75° C. (by means of a heater exchanger not shown in FIG. 1) enters the top of column C1. At the outlet of column C1 (line 16) there is obtained 31.42 kg of maleic anhydride-diisobutylhexahydrophthalate solution with a 10 wt percent maleic anhydride content. In column C1 2.63 kg. of maleic anhydride is absorbed (87.7 percent of the absorbed maleic anhydride); and in column C2 the maleic anhydride absorbed amounts to 0.37 kg (12.3 percent of the absorbed maleic anhydride). There are four theoretical absorption steps (two of which are in column C1 and two in column C2). The solution containing 10 percent of maleic anhydride, is sent to a fractional distillation system (not shown in FIG. 1) wherein practically pure maleic anhydride is obtained as the head product (3.00 kg) and diisobutylhexahydrophthalate, with a 0.5 wt percent maleic anhydride content, as the tail product. The resultant diisobutylhexahydrophthalate is sent back to the absorption system for the maleic anhydride via line 14.

EXAMPLE 4

100.74 kg of off gases, (see FIG. 2) from the catalytic oxidation reaction of n-butane to maleic anhydride, and also containing 2.66 kg of maleic anhydride and 4.82 kg. of water, is sent (line 21) to a partial condensation system working at a temperature of 64° C. Thus, it is possible to recover (line 22) 0.74 kg of maleic anhydride (about 28 percent of the maleic anhydride produced in the reaction phase). The non-condensed gases (100 kg containing 1.92 kg of maleic anhydride) are fed (line 23) to absorption column C1, and are therein washed in a countercurrent manner with dihexylmethyhexahydrophthalate at a temperature of 64° C. The gas leaving column C1 (line 24) only contains 0.05 kg of maleic anhydride. Therefore, the absorption yield is 97.4 percent. The total maleic anhydride recovery yield, considering that 0.74 kg of maleic anhydride is recovered (line 22) in the partial condenser, comes to 98.1 percent. There are three theoretical absorption steps in column C1.

17.72 kg of a mixture of maleic anhydride and dihexylmethylhexahydrophthalate, containing 0.5 wt percent of maleic anhydride, is fed to the top of column C1 (line 25). The solution, rich in maleic anhydride, that is, leaving the bottom of column C1 (line 16), with 10 percent of maleic anhydride content, is sent to a fractional distillation system (not shown in FIG. 2) which yields, as the head product, 1.87 kg of almost pure maleic anhydride and, as the tail product, 17.72 kg of a mixture of maleic anhydride and dihexylmethylhexahydrophthalate having 0.5 wt percent maleic anhydride content. The latter mixture is recycled to the head of column C1 (line 15). Whereas the maleic anhydride obtained by the fractional distillation as the head product is added to the maleic anhydride obtained by partial condensation (line 12) and purified once again by fractional distillation (not shown in FIG. 2) in order to obtain practically pure maleic anhydride.

What is claimed is:

1. In the process for the continuous separation of maleic anhydride from the process gas from the catalytic oxidation of a hydrocarbon in the gaseous phase, which comprises treating the process gases with a solvent, the improvement comprising said solvent being a dialkyl ester, having 4 to 8 carbons in each alkyl group, of hexahydrophthalic acid, tetrahydrophthalic acid, methyltetrahydrophthalic acid or methylhexahydrophthalic acid.

2. Process as claimed in claim 1 wherein said process gases is the reaction gas from the catalytic oxidation of n-butane in the gaseous phase.

3. Process as claimed in claim 2 wherein said solvent is a dialkyl ester, having 4 to 8 carbon atoms in each alkyl group, of hexahydrophthalic acid.

4. Process as claimed in claims 1 or 2 wherein said solvent is dibutyl hexahydrophthalate, diisobutyl tetrahydrophthalate, diisobutyl hexahydrophthalate or dihexyl methylhexahydrophthalate.

* * * * *